US010843987B2

(12) United States Patent
Sun et al.

(10) Patent No.: US 10,843,987 B2
(45) Date of Patent: *Nov. 24, 2020

(54) CATALYTIC CHLORINATION OF 3,3,3-TRIFLUOROPROPENE TO 2,3-DICHLORO-1,1,1-TRIFLUOROPROPANE

(71) Applicant: THE CHEMOURS COMPANY FC, LLC, Wilmington, DE (US)

(72) Inventors: Xuehui Sun, Kennett Square, PA (US); Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/899,990

(22) Filed: Feb. 20, 2018

(65) Prior Publication Data

US 2018/0237364 A1 Aug. 23, 2018

Related U.S. Application Data

(63) Continuation of application No. 15/106,418, filed as application No. PCT/US2014/071114 on Dec. 18, 2014, now Pat. No. 9,938,208.

(60) Provisional application No. 61/917,657, filed on Dec. 18, 2013.

(51) Int. Cl.
| | | |
|---|---|---|
| C07C 17/04 | (2006.01) | |
| B01J 21/18 | (2006.01) | |
| B01J 27/128 | (2006.01) | |
| B01J 27/132 | (2006.01) | |

(52) U.S. Cl.
CPC ............... *C07C 17/04* (2013.01); *B01J 21/18* (2013.01); *B01J 27/128* (2013.01); *B01J 27/132* (2013.01)

(58) Field of Classification Search
CPC ..... C07C 17/04; C07C 17/204; C07C 17/206; C07C 17/25; C07C 19/08; C07C 19/10; C07C 19/12; C07C 21/04; C07C 21/18; B01F 17/0085; C08J 9/144; C08J 9/149; C09K 3/30; C09K 5/045; C09K 21/08
See application file for complete search history.

(56) References Cited

U.S. PATENT DOCUMENTS

| | | |
|---|---|---|
| 6,204,418 B1 | 3/2001 | Stauffer |
| 9,938,208 B2 * | 4/2018 | Sun .................... C07C 17/04 |
| 2011/0031436 A1 | 2/2011 | Mahler et al. |
| 2011/0118513 A1 | 5/2011 | Smith et al. |
| 2011/0124930 A1 | 5/2011 | Smith et al. |
| 2011/0160497 A1 | 6/2011 | Deur-Bert et al. |
| 2011/0160498 A1 | 6/2011 | Pigamo et al. |
| 2011/0237846 A1 | 9/2011 | Kawaguchi et al. |

FOREIGN PATENT DOCUMENTS

| | | |
|---|---|---|
| CN | 102056875 A | 5/2011 |
| CN | 102143930 A | 8/2011 |
| CN | 102336630 A | 2/2012 |
| CN | 103418367 A | 12/2013 |
| JP | 43-8084 A | 3/1968 |
| JP | 60-54904 A | 3/1985 |
| JP | 61-145132 A | 7/1986 |
| JP | 6-510048 A | 11/1994 |
| JP | 2002-273206 A | 9/2002 |
| JP | 2007-105668 A | 4/2007 |
| JP | 2011-516533 A | 5/2011 |
| JP | 2011-517681 A | 6/2011 |
| JP | 2011-520017 A | 7/2011 |
| JP | 2012-502089 A | 1/2012 |
| JP | 2014-210765 A | 11/2014 |
| WO | WO 2009/125200 A2 | 10/2009 |
| WO | 2010/071136 A1 | 6/2010 |

OTHER PUBLICATIONS

First Office Action issued in Chinese Patent Application No. 201480075865.2 dated Apr. 28, 2017 (in English and Chinese).
International Search Report dated Mar. 10, 2015 issued in PCT/US2014/071114.
Second Office Action issued in corresponding Chinese Patent Application No. 201480075865.2 dated Apr. 3, 2018.
Official Notice of Rejection issued in corresponding Japanese Patent Application No. 2016-541625 dated Sep. 25, 2018.
Extended European Search Report for EP Application No. 19217132.0, dated Mar. 20, 2020, 5 pages.

* cited by examiner

*Primary Examiner* — Jafar F Parsa
(74) *Attorney, Agent, or Firm* — McNees Wallace & Nurick LLC

(57) ABSTRACT

The present invention relates to a process for preparing 1,1,1-trifluoro-2,3-dichloropropane which comprises contacting chlorine with 3,3,3-trifluoropropene in the presence of a catalyst to form 1,1,1-trifluoro-2,3-dichloropropane, wherein the catalyst comprises at least one metal halide, where the metal is a metal from Group 13, 14 or 15 of the periodic table or a transition metal or combination thereof.

17 Claims, 2 Drawing Sheets

CATALYTIC CHLORINATION OF 3,3,3-TRIFLUOROPROPENE TO 2,3-DICHLORO-1,1,1-TRIFLUOROPROPANE

CROSS-REFERENCE TO RELATED APPLICATIONS

The present application is a continuation of U.S. application having Serial No. U.S. Ser. No. 15/106,418, filed on Jun. 20, 2016, which is a '371 of International Application having Serial Number PCT/US2014/071114, filed on Dec. 18, 2014, which, in turn, claims benefit of U.S. Provisional application 61/917,657, which was filed on Dec. 18, 2013, the contents of all of which are incorporated by reference.

FIELD OF THE INVENTION

The present invention relates to a process for the production of 2,3-dichloro-1,1,1-trifluoropropane (HCFC-243db) from the chlorination of 3,3,3-trifluoro-1-propene (HFO-1243zf).

BACKGROUND OF THE INVENTION

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for chemical compounds that have both low ozone depleting potentials (ODPs) and low global warming potentials (GWPs).

One such useful HFC that has a low GWP is 2,3,3,3-tetrafluoro-1-propene (HFC-1234yf). It is useful as a refrigerant and blowing agent. It is prepared by many methods, one of which is from the following process:

(1) ($CX_2$=CCl—$CH_2$X or $CX_3$—CCl=$CH_2$ or $CX_3$—CHCl—$CH_2$X)+HF→2-chloro-3,3,3-trifluoropropene (HCFO-1233xf)+HCl in a vapor phase reactor charged with a solid catalyst;

(2) 2-chloro-3,3,3-trifluoropropene (HCFO-1233xf)+HF→2-chloro-1,1,1,2-tetrafluoropropane (HCFC-244bb) in a liquid phase reactor charged with a liquid hydrofluorination catalyst; and (3) 2-chloro-1,1,1,2-tetrafluoropropane (HCFC-244bb)→2,3,3,3-tetrafluoropropene (HFO-1234yf) in a vapor phase reactor.

Thus, 2-chloro-3,3,3-trifluoropropene (HCFO-1233xf) is an intermediate in the process of making 2,3,3,3-tetrafluoropropene (HFO-1234yf). HCFC-1233xf is obtained by the dehydrochlorination of HCFC-243db, the product of the present process.

There have been various methods for preparing HCFC-243db, such as chlorination of 3,3,3-trifluoro-1-propene (HFO-1243zf) with UV light or at high temperatures or in the liquid phase without catalyst. However, there are many problems associated with these methods. The approach with UV light is less selective and difficult to scale-up to a commercial process and the reaction in the liquid phase without a catalyst is very slow and needs to be run at high temperature. Nevertheless, even under these conditions, tar is also formed.

Thus there is a need in the art for a new process to prepare HCFC-243db that does not suffer from the inadequacies of the prior art. The present invention overcomes these problems.

BRIEF SUMMARY OF THE DISCLOSURE

The present process relates to a process for preparing 1,1,1-trifluoro-2,3-dichloropropane which comprises contacting chlorine with 3,3,3-trifluoropropene in the presence of a catalyst to form 1,1,1-trifluoro-2,3-dichloropropane, wherein the catalyst comprises at least one metal halide, where the metal is an element from Group 13, 14 or 15 of the periodic table or is a transition metal or a combination thereof. This reaction can be conducted in the vapor phase or in the liquid phase. The process produces 1,1,1-trifluoro-2,3-dichloropropane in excellent yields and in high selectivity.

BRIEF DESCRIPTION OF THE DRAWINGS

The following figures further illustrate the present invention in a non-limiting way.

DETAILED DESCRIPTION

Figure 1:
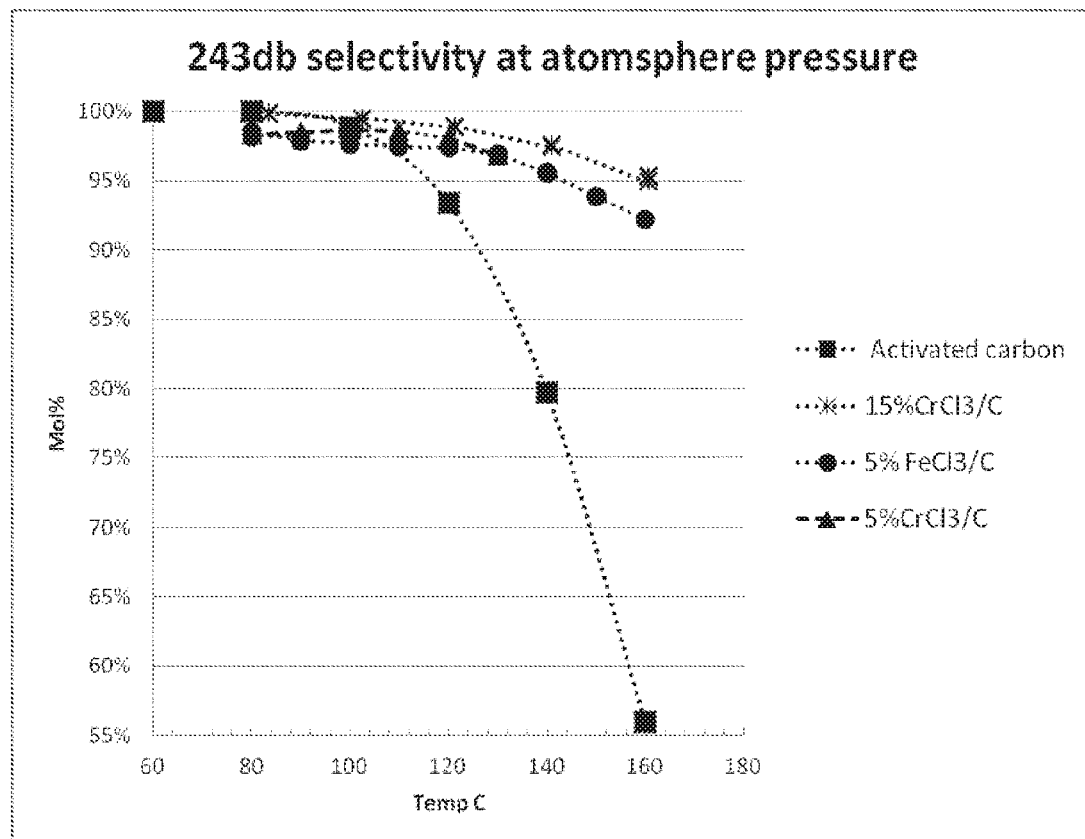
FIG. 1 compares graphically the selectivity of 243db from the chlorination of 1243zf at atmosphere pressure with the following catalysts: activated carbon (Comparative Example 1), 15% $CrCl_3$/C (Example 1), 5% $FeCl_3$/C (Example 3), and 5% $CrCl_3$/C (Example 6).

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Further, reference to values stated in ranges includes each and every value within that range.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publication, patent applications, patents, and other references mentioned herein are incorporated by reference in their entirety, unless a particular passage is cited. In case of conflict, the present specification, including definitions, will control. In addition, the materials, methods, and examples are illustrative only and not intending to be limiting.

Many aspects and embodiments are described herein, and are merely exemplary, not limiting. After reading this specification, skilled artisans will appreciate that other aspects and embodiments are possible without departing from the scope of the invention. Other features and benefits of any one or more of the embodiments will be apparent from the following detailed description, and from the claims.

As described hereinabove, the present process relates to a chlorination of 3,3,3-trifluoropropene in the presence of a catalyst to form 1,1,1-trifluoro-2,3-dichloropropane, wherein the catalyst comprises at least one metal halide, where the metal is a metal from Group 13, 14 or 15 of the periodic table or a transition metal.

As used herein, the term "halide" refers to fluorides, chlorides, bromides and iodides.

The term metal, as used herein, refers to the metals of the periodic table. They exclude the non-metals, halogens, noble gases, and actinides. However, as used herein, the term metal includes metalloids. Examples of metals include the metals in Groups 13 and 14 of the periodic table. The term also includes the transition metals as defined herein. Examples of metals include nickel, chromium, iron, scandium, yttrium, lanthanum, titanium, zirconium, hafnium, vanadium, molybdenum, tungsten, manganese, rhenium, ruthenium, osmium, cobalt, palladium, copper, zinc, tantalum, antimony, aluminum, tin, and lead. It is to be noted, as defined herein, antimony is a metalloid, and by the definition herein, is a metal.

The term "transition metal" refers to the elements in the columns 3, 4, 5, 6, 7, 8, 9, 10, 11, and 12, including the lanthanides. Examples of transition metals include nickel, chromium, iron, scandium, yttrium, lanthanum, titanium, zirconium, hafnium, vanadium, molybdenum, tungsten, manganese, rhenium, ruthenium, osmium, cobalt, palladium, copper, zinc, and tantalum.

Since the catalyst used in the chlorination reaction described herein is in the form of a metal halide, the metal used herein have positive oxidation numbers of +1, +2, +3, +4 or +5, depending on the identity of the metal that forms the salt with the halide.

The term "activated carbon" includes any carbon with a relatively high surface area such as from about 50 to about 3000 $m^2$ or from about 100 to about 2000 $m^2$ (e.g. from about 200 to about 1500 $m^2$ or about 300 to about 1000 $m^2$). The activated carbon may be derived from any carbonaceous material, such as coal (e.g. charcoal), nutshells (e.g. coconut) and wood. Any form of activated carbon may be used, such as powdered, granulated and pelleted activated carbon. Activated carbon which has been modified (e.g. impregnated) by the addition of Cr, Mn, Au, Fe, Sn, Ta, Ti, Sb, Al, Co, Ni, Mo, Ru, Rh, Pd and/or Pt and/or a compound (e.g. a halide) of one or more of these metals may be used.

In some embodiments, the activated carbon has been washed with at least one basic solution to remove silicates. For example, the activated carbon is washed with alkali hydroxide or alkaline earth hydroxide or ammonium hydroxide. Examples of basic solutions which have been used to wash the activated carbon include sodium hydroxide, ammonium hydroxide, potassium hydroxide, and the like.

In addition, other suitable forms of activated carbon include but are not limited to acid washed activated carbon powders made by steam activation of lignite coal. In some embodiments, organic and/or inorganic nitrogen containing acids, such as nitric acid, are used. Additional acids that may be used include, but are not limited to, sulfuric, hydrochloric, phosphoric and combinations thereof. The acid preferably has an aqueous concentration between 2 and 12 mol/l. According to one aspect, the activated carbon is soaked for at least 1 hour, such as 1-36 hours, for example 1-10 hours. Optionally, the activated carbon may be agitated during soaking. If desired, the activated carbon may be rinsed in deionized water after the washing to increase the pH to 5-8. In some embodiments, the activated carbon has been washed with at least one acid and at least one base to reduce calcined ash and remove silicates.

The metal halides used as catalysts are metals in Groups 13 and 14 of the periodic table as well as transition metals and the metalloid antimony. Examples of metals include nickel, chromium, iron, scandium, yttrium, lanthanum, titanium, zirconium, hafnium, vanadium, molybdenum, tungsten, manganese, rhenium, ruthenium, osmium, cobalt, palladium, copper, zinc, tantalum, aluminum, tin, and lead. It is to be noted, as defined herein, antimony is a metalloid. However, as defined herein, metalloids are included in the definition of metals. Examples of metal halides include nickel halides, chromium halides, iron halides, scandium halides, yttrium halides, lanthanum halides, titanium halides, zirconium halides, hafnium halides, vanadium halides, molybdenum halides, tungsten halides, manganese halides, rhenium halides, ruthenium halides, osmium halides, cobalt halides, palladium halides, copper halides, zinc halides, antimony halides, tantalum halides, aluminum halides, tin halides, and lead halides. In an embodiment, the metal halide is nickel halide, iron halide, or chromium halide or combination thereof is used as a catalyst with or without support on activated carbon. In another embodiment, the metal halide is a bromide or chloride. In still another embodiment, the halide is a chloride. In another embodiment, the metal halide is nickel chloride, iron chloride, or chromium chloride or combination thereof.

The catalysts of the present chlorination process, the metal halides, may be unsupported or supported on activated carbon. The activated carbon may be unwashed or be acid washed or base washed.

For the chlorination reaction, the chlorine is present in the gaseous state. Either chlorine gas is used or chlorine gas is generated in situ from the reaction of hydrogen chloride in the gaseous state and oxygen.

In an embodiment, the chlorination reaction is conducted in the absence of water. If water is present, it is present in less than 1% by weight in an embodiment, or in another embodiment, less than 0.5% by weight.

3,3,3-Trifluoropropene is commercially available. Alternatively, it can be prepared using techniques known in the art. See, for example, U.S. Patent Publication No. 2011/0118513 to Smith et al., the contents of which are incorporated by reference.

As described hereinbelow, the chlorination reaction may be conducted in either the vapor or liquid phase.

If conducted in the vapor phase, the process is conducted at effective temperatures and pressures. In an embodiment, the reaction is conducted at a temperature ranging from about 80 to about 200° C. In another embodiment, the process is conducted at a temperature ranging from 80 to about 160° C. In still another embodiment, the chlorination reaction is conducted at a temperature ranging from about 80 to about 130° C., and in another embodiment from about 80 to about 120° C. The process may be conducted at a pressure ranging from about 10 psig to about 100 psig. In another embodiment, the pressure ranges from about 1 atmosphere to about 50 psig, and in another embodiment, the pressure ranges from about 20 to about 50 psig. Thus, in an embodiment the process is conducted in the vapor phase at a temperature ranging from about 80 to about 200° C. and at a pressure ranging from about 10 to about 100 psig, and in another embodiment from about 1 atmosphere to about 50 psig and in another embodiment, from about 10 to about 50 psig, e.g., about 20 to about 50 psig. In another embodiment, the chlorination reaction described above is conducted at a temperature ranging from about 80 to about 160° C. and a pressure ranging from about 10 to about 100 psig, and in another embodiment from about 1 atmosphere to about 50 psig and in another embodiment, from about 20 to about 50 psig. In a further embodiment the chlorination reaction is conducted at a temperature ranging from about 80 to 130° C. at a pressure ranging from about 10 to about 100 psig, and in another embodiment, from about 1 atmosphere to about 50 psig and in another embodiment from about 20 to about 50 psig.

The 3,3,3-trifluoropropene and chlorine gas are present in amounts that are effective for the chlorination reaction to occur. The molar amount of 3,3,3-trifluoropropene is present, in one embodiment, in excess of the molar amount of chlorine gas. In an embodiment, the molar ratio of 3,3,3-trifluoropropene to chlorine gas ranges from about 1:0.02 to about 1:1. In another embodiment, the molar ratio of 3,3,3-trifluoropropene to chlorine gas ranges from about 1:0.1 to about 1:0.8. In still another embodiment, the mole ratio of 3,3,3-trifluoropropene to chlorine gas ranges from about 1:0.1 to about 1:0.5.

The contact time for the chlorination reaction, i.e., the time of the reaction to occur, may range from about 0.1 second to about 120 seconds, and in another embodiment, from about 5 seconds to about 1 minute. However, longer or shorter times can be used. As used herein, the contact time is determined by the following equation:

$$\text{Contact time in seconds} = 1/((\text{Total Gas Flow in SCCM})/60/\text{Cat vol})) \times (14.7 + P \text{ in PSIG})/14.7 \times (298/(273 + T° C.)),$$

wherein SCCM is standard cubic centimeters per minute, P is pressure, PSIG is operating pressure in pounds per square inch-gauge pressure not absolute pressure, T° C. is temperature in degrees Centigrade, and the catalyst volume in cubic centimeters.

The metal halide catalyst is present in the chlorination reaction in the vapor phase in catalytic effective amounts. In an embodiment, it is loaded on activated carbon, which is unwashed or washed with acid or base. In an embodiment the metal halide is loaded on activated carbon and is present in an amount ranging from about 2 to about 30 wt %, and in another embodiment, from about 3 to about 25 wt % and in another embodiment from about 5 to about 20 wt % of the activated carbon.

In an embodiment, the chlorination reaction is carried out to attain a conversion of about 50% or higher, preferably, about 90% or higher. Conversion is calculated by the number of moles of reactant (mole ratio of 3,3,3-trifluoropropene)) consumed divided by number of moles of reactant (mole ratio of 3,3,3-trifluoropropene) fed to the reactor multiplied by 100. The selectivity for 1,1,1-trifluoro-2,3-dichloropropane attained is preferably about 60% or higher and more preferably about 80% or higher. Selectivity is calculated by number of moles of product (1,1,1-trifluoro-2,3-dichloropropane) formed divided by number of moles of reactant consumed.

The present process in the gas phase provides higher 243db selectivity than activated carbon by itself at the higher temperatures, such as from 100 to 160° C. and in another embodiment from about 120 to about 200° C. Thus, at these temperatures ranges, the chlorination reaction can be conducted at a pressure ranging from vacuum to about 100 psig, and in another embodiment, from about 1 atmosphere to about 50 psig and in another embodiment, from about 10 psig to about 50 psig. The present process is able to operate at higher back pressures above the dew point of 243db.

This chlorination reaction may be conducted in any reactor suitable for a vapor phase chlorination reaction. In certain embodiments, the reactor is constructed from materials which are resistant to the corrosive effects of chlorine and catalyst such as Hastalloy, Inconel, Monel and fluoropolymer linings. The vessel is a fixed catalyst bed or fluidized bed. If desired, inert gases such as nitrogen or argon may be employed in the reactor during operation.

In an embodiment the catalyst in the vapor phase reaction is supported on activated carbon which may be unwashed or may be acid washed or base washed, as indicated hereinabove.

In another embodiment, the chlorination reaction is conducted in the liquid phase. The present process in the liquid phase may be carried out in any suitable apparatus, such as a static mixer, a tubular reactor or a stirred vapor-liquid disengagement vessel. This apparatus, in one embodiment, described herein is made from one or more material that are resistant to corrosion, e.g., stainless steels, in particular of the austenitic type, the well-known high nickel alloys, such as Monel™ nickel-copper alloys, Hastelloy™ nickel-based alloys, and Inconel™ nickel-chromium alloys, and copper-clad steel. The present process may be carried out batchwise or continuously.

Vigorous shaking, agitation, and/or stirring may be needed to effect the completion of the reaction. The extent of agitation depends on the desired reaction rate and which, in turn, is dependent on the reactor geometry, residence time, agitator and baffle design and solubility of 3,3,3-trifluoropropene in the solvent. Thus, the chlorination reaction in the liquid phase is conducted with stirring.

In the liquid phase, the chlorination reaction can be conducted with or without an inert solvent in which the 3,3,3-trifluoropropene is soluble and can be easily separated from the 3,3,3-trifluoropropene and the 1,1,1-trifluoro-2,3-dichloropropane. The term "inert" means that the solvent does not react with chlorine, 3,3,3-trifluoropropene or 1,1,1-trifluoro-2,3-dichloropropane under the reaction condition described herein. Examples of suitable solvents include carbon tetrachloride, 1,1,2-trichloro-1,2,2-trifluoroethane, a $C_{5-8}$ linear perfluoroalkyl compound represented by $CF_3(CF_2)_nCF_3$, where n is an integer from 3 to 6, inclusive, or a perhalogenated compound, such as hexachloracetone, and 1,1,1-trifluoro-2,3-dichloropropane, and the like.

The amount of solvent to be used for the reaction in the chlorination step is not particularly limited so long as the 3,3,3-trifluoropropene can thereby be dissolved. In an embodiment, the amount of solvent present ranges from about 1 to about 1000 mass %, and in another embodiment, from about 50 to about 100 mass %, based on the raw material components (the total amount of 3,3,3-trifluoropropene and chlorine).

The catalyst used herein may be heterogeneous or partially dissolved in the liquid phase containing 3,3,3-trifluoro-1-propene/2,3-dichloro-1,1,1-trifluoropropane (1243zf/243db). In another embodiment, the catalyst is a homogenous catalyst.

The reaction is conducted in effective amounts of chlorine gas and 3,3,3-trifluoropropene to form 1,1,1-trifluoro-2,3-dichloropropane. As in the vapor phase reaction, the molar amount of 3,3,3-trifluoropropene is present, in one embodiment, in excess of the molar amount of chlorine gas. In an embodiment, the molar ratio of 3,3,3-trifluoropropene to chlorine ranges from about 1:0.02 to about 1:1, and in another embodiment, from about 1:0.1 to 1:0.9 and in another embodiment, from about 1:0.1 to about 1:0.95.

The chlorination reaction is conducted at an effective temperature. In an embodiment, the effective temperature ranges from about 20 to about 200° C., while in another embodiment, from about 30 to about 110° C. and in another embodiment, from about 35 to about 90° C.

The reactor pressure in the liquid phase process is not critical and in batch reactions is usually the autogenous pressure of the system at the reaction temperature.

The metal halide catalyst in the liquid phase is present in catalytic effective amounts. In an embodiment the catalyst is not supported. In a embodiment, it is present in an amount ranging from about 0.1 to 10 wt % of the reactants (that is, total weight of chlorine and 3,3,3-trifluoropropene), and in another embodiment from about 0.5 to about 6 wt % and in another embodiment from about 1 to about 4 wt %.

The reaction time for the chlorination reaction in the liquid phase may vary over a wide range. However, the reaction time will typically be in the range of about 0.01 to about 100 hours, for example, from about 0.5 hours to about 50 hours.

The chlorination reaction in both the liquid phase and the vapor phase is preferably carried out to attain a conversion of about 50% or higher, preferably, about 90% or higher. As described hereinabove, the reaction is conducted, in an embodiment, when the molar amount of 3,3,3-trifluoropropene is equal or greater than chlorine. Conversion is calculated by the number of moles of reactant (mole ratio of 3,3,3-trifluoropropene) consumed divided by number of moles of reactant (mole ratio of 3,3,3-trifluoropropene) fed to the reactor multiplied by 100. The selectivity for 1,1,1-trifluoro-2,3-dichloropropane attained is preferably about 60% or higher and more preferably about 80% or higher. Selectivity is calculated by number of moles of product (1,1,1-trifluoro-2,3-dichloropropane) formed divided by number of moles of reactant consumed.

Regardless of whether the reaction is conducted in the gas phase or liquid phase, the 1,1,1-trifluoro-2,3-dichloropropane is isolated, i.e. separately collected. The product comprising 1,1,1-trifluoro-2,3-dichloropropane is removed from the reactor by techniques known in the art, such as siphoning and is collected. In the case of gas phase, the product flows out of the reactor and is condensed. The product comprising 1,1,1-trifluoro-2,3-dichloropropane is purified by techniques known in the art, such as distillation. The present process, whether conducted in the gaseous phase or in the liquid phase, can be utilized commercially and is easily scaled up for commercial production. In addition, the rate of the chlorination reaction using the process described herein provides a higher conversion and selectivity with a faster rate of reaction than processes used heretofore for the chlorination of 3,3,3-trifluoropropene to 1,1,1-trifluoro-2,3-dichloropropane.

In both the vapor phase and liquid phase chlorination reactions there are several side reactions competing with the formation of the product 2,3-dichloro-1,1,1-trifluoropropane (HCFC243db). These side reactions include the following:

a. the conversion of 243db to 1,1,1-trifluoro-3-chloropropylene;

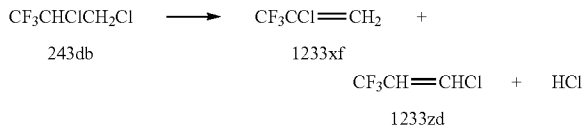

b. the conversion of 1233xf to 233ab;

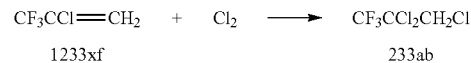

c. the conversion of 1233zd to 233da;

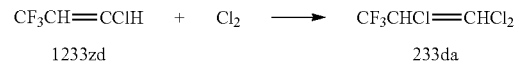

d. the formation of 1223xd;

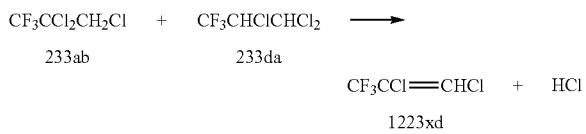

e. the formation of 223aa from 1223xd

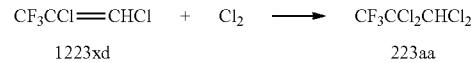

f. the conversion of 223aa to 1213xa;

g. the conversion of 1213xa to 213ab

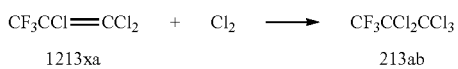

1213xa → 213ab h. the conversion of 243db to 244db and 242dc

213ab → 244db + CF$_2$ClCHClCH$_2$Cl (242dc)

In addition, although not present in the vapor phase, in the liquid phase chlorination reaction, there is possibility of oligomerization and the formation of black tar.

Yet, despite all of these side reactions, the selectivity and conversion utilizing the present process is surprisingly high.

Further, the formation of the product can be confirmed by installing analytical equipment, such as gas chromatography on the reaction apparatus and carrying out the continuous measurement.

In an embodiment, anhydrous HCl, such as HCl(g), is cofed with the 3,3,3-tri-fluoropropene in both the vapor and liquid phase reactions. The added HCl suppresses the side reactions and helps to manage the high heat formation as a diluent. In an embodiment, the HCl is present in an amount ranging from about 0.5% to about 20 mol % and in another embodiment from about 1 to about 10 mol % and in another embodiment from about 1.5 to about 5 mol % relative to the amount of 1243zf present.

Without further elaboration, one skilled in the art, using the description herein, can utilize the present invention to its fullest extent. The following specific embodiments are, therefore, to be construed as merely illustrative, and do not constrain the remainder of the disclosure in any way whatsoever.

The following non-limiting examples further illustrate the present invention.

EXAMPLES

Example 1: Chlorination of 1243zf with 5% CrCl$_3$ Loaded Acid Washed Activated Carbon at Atmosphere Pressure 2 ml 12-20 mesh 5% CrCl$_3$/C catalyst was loaded into a ½ inch Monel reactor. The catalyst was dried at 200° C. under 100 sccm N$_2$ for one hour, then 1243zf and Cl$_2$ was fed from the top of the reactor at atmosphere pressure. The stream from the reactor was analyzed by GC and GC-MS. The results of the test are shown in Table 1. The catalyst showed great activity and selectivity.

TABLE 1

| Reactor Temp ° C. | 1243zf flow rate sccm | Cl$_2$ flow rate sccm | 1243zf conversion mol % | 243db selectivity mol % | Backpressure psig |
|---|---|---|---|---|---|
| 80 | 39.78 | 8.30 | 14.81% | 98.30% | 0.69 |
| 90 | 39.84 | 7.92 | 15.92% | 98.46% | 0.69 |
| 100 | 39.93 | 7.87 | 16.69% | 98.64% | 0.69 |
| 110 | 39.58 | 8.00 | 17.17% | 98.57% | 0.69 |

TABLE 1-continued

| Reactor Temp ° C. | 1243zf flow rate sccm | Cl$_2$ flow rate sccm | 1243zf conversion mol % | 243db selectivity mol % | Backpressure psig |
|---|---|---|---|---|---|
| 120 | 39.89 | 7.79 | 17.40% | 98.03% | 0.69 |
| 130 | 40.06 | 7.90 | 17.43% | 96.90% | 0.69 |
| 80 | 31.90 | 15.51 | 29.93% | 98.19% | 0.69 |
| 90 | 31.94 | 15.77 | 33.24% | 98.31% | 0.69 |
| 100 | 31.91 | 15.73 | 36.14% | 98.45% | 0.69 |
| 110 | 31.64 | 15.70 | 38.47% | 98.42% | 0.69 |
| 120 | 31.91 | 15.65 | 40.12% | 97.81% | 0.69 |
| 130 | 31.59 | 15.33 | 41.03% | 96.44% | 0.69 |

Example 2: Chlorination of 1243zf with 5% CrCl$_3$ Loaded Acid Washed Activated Carbon at 25 Psig 2 ml 12-20 mesh 5% CrCl$_3$/C catalyst was loaded into a ½ inch Monel reactor. The catalyst was dried at 200° C. under 100 sccm N$_2$ for one hour, then 1243zf and Cl$_2$ was fed from the top of the reactor at 25 psig. The stream from the reactor was analyzed by GC and GC-MS. The results are shown in Table 2. The catalyst showed great activity and selectivity at 25 psig.

TABLE 2

| Reactor Temp ° C. | 1243zf flow rate sccm | Cl$_2$ flow rate sccm | 1243zf conversion mol % | 243db selectivity mol % | Backpressure psig |
|---|---|---|---|---|---|
| 80 | 39.97 | 8.28 | 17.38% | 98.36% | 25.00 |
| 90 | 40.11 | 8.28 | 17.69% | 98.74% | 25.00 |
| 100 | 39.87 | 7.99 | 17.95% | 98.88% | 25.00 |
| 110 | 40.15 | 7.93 | 17.95% | 98.72% | 25.00 |
| 120 | 39.86 | 8.05 | 17.88% | 98.14% | 25.00 |
| 130 | 40.07 | 8.17 | 18.08% | 96.99% | 25.00 |
| 90 | 31.90 | 15.50 | 43.48% | 97.88% | 25.00 |
| 100 | 32.11 | 15.73 | 44.46% | 98.09% | 25.00 |
| 110 | 32.35 | 15.48 | 45.12% | 98.00% | 25.00 |
| 120 | 32.07 | 15.95 | 44.99% | 97.36% | 25.01 |
| 130 | 31.98 | 15.64 | 45.20% | 96.13% | 25.00 |
| 140 | 31.98 | 15.64 | 44.88% | 94.02% | 25.00 |
| 150 | 31.98 | 15.64 | 44.65% | 91.02% | 25.00 |

Example 3: Chlorination of 1243zf with 15% CrCl$_3$ Loaded Acid Washed Activated Carbon at Atmosphere Pressure 5 ml 12-20 mesh 15% CrCl$_3$/C catalyst was loaded into a ½ inch Monel reactor. The catalyst was dried at 200° C. under 100 sccm N$_2$ for one hour, then 1243zf and Cl$_2$ was fed from the top of the reactor at atmosphere pressure. The stream from the reactor was analyzed by GC and GC-MS. The results of the test are shown in Table 3. The catalyst showed great activity and selectivity.

TABLE 3

| Reactor Temp ° C. | 1243zf flow rate sccm | Cl$_2$ flow rate sccm | 1243zf conversion mol % | 243db selectivity mol % | Backpressure psig |
|---|---|---|---|---|---|
| 80 | 25.26 | 4.97 | 17.29% | 99.80% | 0.80 |
| 100 | 23.40 | 5.23 | 18.85% | 99.49% | 0.79 |
| 120 | 24.89 | 5.09 | 19.01% | 98.90% | 0.80 |
| 140 | 24.78 | 5.27 | 19.05% | 97.55% | 0.79 |
| 160 | 24.92 | 5.03 | 18.99% | 95.37% | 0.79 |
| 80 | 20.38 | 10.15 | 34.74% | 99.83% | 0.79 |
| 100 | 19.74 | 9.77 | 43.91% | 99.57% | 0.79 |
| 120 | 20.45 | 9.44 | 46.76% | 99.06% | 0.79 |

TABLE 3-continued

| Reactor Temp °C. | 1243zf flow rate sccm | Cl₂ flow rate sccm | 1243zf conversion mol % | 243db selectivity mol % | Backpressure psig |
|---|---|---|---|---|---|
| 140 | 20.29 | 9.68 | 47.10% | 97.80% | 0.79 |
| 160 | 20.31 | 9.68 | 46.62% | 95.13% | 0.80 |

Example 4: Chlorination of 1243zf with 15% $CrCl_3$ Loaded Acid Washed Activated Carbon at 25 Psig 5 ml 12-20 mesh 15% $CrCl_3$/C catalyst was loaded into a ½ inch Monel reactor. The catalyst was dried at 200° C. under 100 sccm $N_2$ for one hour, then 1243zf and $Cl_2$ was fed from the top of the reactor at 25 psig. The stream from the reactor was analyzed by GC and GC-MS. The results are shown in Table 4. The catalyst showed great activity and selectivity.

TABLE 4

| Reactor Temp °C. | 1243zf flow rate sccm | Cl₂ flow rate sccm | 1243zf conversion mol % | 243db selectivity mol % | Backpressure psig |
|---|---|---|---|---|---|
| 80 | 39.64 | 8.32 | 18.09% | 99.51% | 25.01 |
| 90 | 39.76 | 8.13 | 18.40% | 99.53% | 25.20 |
| 100 | 39.61 | 7.82 | 17.93% | 99.38% | 25.10 |
| 110 | 39.94 | 8.21 | 18.10% | 99.15% | 24.81 |
| 80 | 31.68 | 15.75 | 40.66% | 99.56% | 24.80 |
| 90 | 31.67 | 15.98 | 43.09% | 99.50% | 24.80 |
| 100 | 32.47 | 15.77 | 45.80% | 99.38% | 25.29 |
| 110 | 31.55 | 15.32 | 44.74% | 99.16% | 24.80 |

Example 5: Chlorination of 1243zf with 15% $CrCl_3$ Loaded Acid Washed Activated Carbon at 40 Psig 2 nil 12-20 mesh 15% $CrCl_3$/C catalyst was loaded into a ½ inch Monel reactor. The catalyst was dried at 200° C. under 100 sccm $N_2$ for one hour, then 1243zf and $Cl_2$ was fed from the top of the reactor at 40 psig. The stream from the reactor was analyzed by GC and GC-MS. The results are shown in Table 5. The catalyst shows great activity and selectivity.

TABLE 5

| Reactor Temp °C. | 1243zf flow rate sccm | Cl₂ flow rate sccm | 1243zf conversion mol % | 243db selectivity mol % | Backpressure psig |
|---|---|---|---|---|---|
| 80 | 40.00 | 8.30 | 17.36% | 97.35% | 39.80 |
| 90 | 40.00 | 8.30 | 18.55% | 98.15% | 40.20 |
| 100 | 40.00 | 8.30 | 17.73% | 98.43% | 39.80 |
| 110 | 39.99 | 7.90 | 18.17% | 98.35% | 39.90 |
| 120 | 40.31 | 7.86 | 18.66% | 98.18% | 40.00 |
| 130 | 40.09 | 8.30 | 18.66% | 97.61% | 40.00 |
| 140 | 40.01 | 7.93 | 18.40% | 96.77% | 40.00 |
| 150 | 40.16 | 8.07 | 18.67% | 95.52% | 39.90 |
| 160 | 40.29 | 7.87 | 18.67% | 93.51% | 40.10 |
| 100 | 31.90 | 15.34 | 45.90% | 96.69% | 40.10 |
| 110 | 31.90 | 15.69 | 47.09% | 96.79% | 39.90 |
| 120 | 31.59 | 15.47 | 46.83% | 96.79% | 40.00 |
| 130 | 31.66 | 15.62 | 47.20% | 96.27% | 40.00 |
| 140 | 32.38 | 15.72 | 47.25% | 95.11% | 40.00 |
| 150 | 31.61 | 15.78 | 47.21% | 93.49% | 40.00 |

Example 6: Chlorination of 1243zf with 5% $FeCl_3$ Loaded Acid Washed Activated Carbon at Atmosphere Pressure 2 ml 12-20 mesh 5% FeCl3/C catalyst was loaded into a ½ inch Monel reactor. The catalyst was dried at 200° C. under 100 sccm $N_2$ for one hour, then 1243zf and $Cl_2$ was fed from the top of the reactor at atmosphere pressure. The stream from the reactor was analyzed by GC and GC-MS. The results are shown in Table 6. The catalyst shows great activity and selectivity.

TABLE 6

| Reactor Temp °C. | 1243zf flow rate sccm | Cl₂ flow rate sccm | 1243zf conversion mol % | 243db selectivity mol % | Backpressure psig |
|---|---|---|---|---|---|
| 80 | 39.34 | 7.92 | 11.38% | 98.31% | 0.69 |
| 90 | 39.29 | 8.01 | 13.42% | 97.85% | 0.69 |
| 100 | 39.74 | 8.01 | 14.68% | 97.57% | 0.69 |
| 110 | 39.73 | 8.01 | 15.86% | 97.43% | 0.70 |
| 120 | 39.43 | 8.33 | 16.82% | 97.38% | 0.80 |
| 130 | 39.52 | 7.96 | 17.47% | 96.89% | 0.69 |
| 140 | 39.09 | 8.04 | 17.84% | 95.60% | 0.80 |
| 150 | 39.68 | 8.04 | 17.99% | 93.84% | 0.79 |
| 160 | 39.72 | 8.02 | 0.81% | 0.00% | 0.69 |
| 80 | 31.98 | 15.93 | 24.00% | 98.32% | 0.69 |
| 90 | 31.90 | 15.71 | 26.73% | 97.80% | 0.69 |
| 100 | 31.57 | 15.53 | 29.56% | 97.32% | 0.69 |
| 110 | 31.99 | 15.62 | 32.33% | 97.04% | 0.69 |
| 120 | 31.78 | 15.60 | 35.28% | 96.99% | 0.69 |
| 130 | 31.74 | 15.38 | 37.73% | 96.59% | 0.79 |
| 140 | 31.63 | 15.32 | 39.69% | 94.23% | 0.79 |
| 150 | 31.91 | 15.53 | 41.32% | 90.71% | 0.79 |

Example 7: Chlorination of 1243zf with 5% $FeCl_3$ Loaded Acid Washed Activated Carbon at 25 Psig 2 ml 12-20 mesh 5% $FeCl_3$/C catalyst was loaded into a ½ inch Monel reactor. The catalyst was dried at 200° C. under 100 sccm $N_2$ for one hour, then 1243zf and $Cl_2$ was fed from the top of the reactor at 25 psig. The stream from the reactor was analyzed by GC and GC-MS. The results are shown in Table 7. The catalyst shows great activity and selectivity.

TABLE 7

| Reactor Temp °C. | 1243zf flow rate sccm | Cl₂ flow rate sccm | 1243zf conversion mol % | 243db selectivity mol % | Backpressure psig |
|---|---|---|---|---|---|
| 80 | 39.02 | 7.67 | 17.52% | 95.31% | 25.00 |
| 90 | 39.51 | 7.94 | 17.94% | 95.82% | 25.01 |
| 100 | 39.29 | 7.94 | 18.05% | 96.51% | 25.00 |
| 110 | 35.64 | 7.91 | 19.89% | 97.21% | 25.01 |
| 80 | 31.57 | 15.63 | 41.66% | 94.48% | 25.00 |
| 90 | 32.21 | 15.64 | 42.78% | 94.32% | 25.00 |
| 100 | 32.23 | 15.28 | 44.04% | 94.54% | 24.99 |

Example 8: Chlorination of 1243zf with 12.6% $FeCl_3$ Loaded Acid Washed Activated Carbon at Atmosphere Pressure 2 ml 12-20 mesh 12.6% $FeCl_3$/C catalyst was loaded into a ½ inch Monel reactor. The catalyst was dried at 200° C. under 100 sccm $N_2$ for one hour, then 1243zf and $Cl_2$ was fed from the top of the reactor at atmosphere pressure. The stream from the reactor was analyzed by GC and GC-MS. The results are shown in Table 8. The catalyst shows great activity and selectivity.

TABLE 8

| Reactor Temp ° C. | 1243zf flow rate sccm | Cl₂ flow rate sccm | 1243zf conversion mol % | 243db selectivity mol % | Backpressure psig |
|---|---|---|---|---|---|
| 80 | 39.70 | 7.61 | 17.34% | 95.41% | 0.69 |
| 90 | 39.44 | 7.99 | 17.83% | 95.07% | 0.69 |
| 100 | 39.84 | 7.78 | 18.12% | 94.67% | 0.69 |
| 110 | 39.43 | 7.98 | 18.33% | 94.47% | 0.69 |
| 120 | 39.84 | 7.89 | 18.51% | 94.40% | 0.69 |
| 130 | 39.53 | 8.28 | 18.45% | 94.81% | 0.69 |
| 140 | 39.70 | 8.22 | 18.50% | 95.06% | 0.69 |
| 80 | 31.98 | 15.56 | 39.45% | 93.70% | 0.69 |
| 90 | 31.89 | 15.32 | 41.33% | 92.14% | 0.69 |
| 100 | 31.90 | 15.78 | 43.16% | 90.27% | 0.69 |
| 110 | 32.02 | 15.52 | 43.96% | 89.46% | 0.69 |
| 120 | 31.69 | 15.38 | 44.65% | 89.37% | 0.69 |
| 130 | 32.11 | 15.72 | 43.55% | 92.03% | 0.69 |
| 140 | 31.61 | 15.72 | 43.70% | 92.19% | 0.69 |

Example 9: Chlorination of 1243zf with 30% FeCl3 Loaded Acid Washed Activated Carbon at Atmosphere Pressure 5 ml 12-20 mesh 30% FeCl₃/C catalyst was loaded into a ½ inch Monel reactor. The catalyst was dried at 200° C. under 100 sccm N₂ for one hour, then 1243zf and Cl₂ was fed from the top of the reactor at atmosphere pressure. The stream from the reactor was analyzed by GC and GC-MS. The results are shown in Table 9. The catalyst shows great activity and selectivity.

TABLE 9

| Reactor Temp ° C. | 1243zf flow rate sccm | Cl₂ flow rate sccm | 1243zf conversion mol % | 243db selectivity mol % | Backpressure psig |
|---|---|---|---|---|---|
| 100 | 24.91 | 5.31 | 11.73% | 99.45% | 0.90 |
| 120 | 25.12 | 5.05 | 15.49% | 99.11% | 0.80 |
| 140 | 24.89 | 5.29 | 18.84% | 97.89% | 0.79 |
| 160 | 24.89 | 5.23 | 19.50% | 96.55% | 0.81 |
| 100 | 20.35 | 9.79 | 19.18% | 99.68% | 0.79 |
| 120 | 20.32 | 9.65 | 27.88% | 99.22% | 0.79 |
| 140 | 20.11 | 9.77 | 37.23% | 97.82% | 0.79 |
| 160 | 20.40 | 9.92 | 45.73% | 94.07% | 0.79 |
| 100 | 15.68 | 13.62 | 26.68% | 99.59% | 0.79 |
| 120 | 16.40 | 13.48 | 37.83% | 99.21% | 0.80 |
| 140 | 16.33 | 13.50 | 50.30% | 97.82% | 0.80 |
| 160 | 16.10 | 13.75 | 67.11% | 90.52% | 0.80 |
| 100 | 31.56 | 15.34 | 16.43% | 99.45% | 0.80 |
| 120 | 31.86 | 15.60 | 22.96% | 99.17% | 0.80 |
| 140 | 31.40 | 15.29 | 30.99% | 97.97% | 0.80 |

Comparative Example 1: Chlorination of 1243zf with Acid Washed Activated Carbon at Atmosphere Pressure 5 ml 12-20 mesh carbon catalyst was loaded into a ½ inch Monel reactor. The catalyst was dried at 200° C. under 100 sccm N₂ for one hour, then 1243zf and Cl₂ was fed from top of the reactor at atmosphere pressure. The stream from the reactor was analyzed by GC and GC-MS. The results are shown in Table 10. The catalyst shows great activity and but lower selectivity.

TABLE 10

| Reactor Temp ° C. | 1243zf flow rate sccm | Cl₂ flow rate sccm | 1243zf conversion mol % | 243db selectivity mol % | Backpressure psig |
|---|---|---|---|---|---|
| 60 | 25.23 | 4.80 | 13.60% | 100.00% | 0.79 |
| 80 | 24.52 | 5.25 | 18.56% | 100.00% | 0.79 |
| 100 | 24.64 | 5.25 | 19.05% | 98.84% | 0.79 |
| 120 | 24.74 | 5.18 | 18.98% | 93.33% | 0.79 |
| 140 | 24.88 | 5.26 | 18.24% | 79.69% | 0.79 |
| 160 | 24.61 | 5.07 | 17.14% | 55.95% | 0.80 |

FIG. 1 compares the 243db selectivity over a temperature range of 60° C. to 180° C. at atmosphere pressure with respect to the chlorination of 3,3,3-trifluoropropene in the vapor phase reaction utilizing activated carbon as the catalyst (Comparative Example 1) 15% CrCl₃/C as the catalyst (Example 1), 5% FeCl2/C as the catalyst (Example 3), and 5% CrCl₃/C as the catalyst (Example 6). As clearly shown the selectivity of 243db begins to drop off at about 100° C. when activated carbon is the catalyst, and drops off dramatically at about 120° C., while the metal halides supported on activated carbon maintain a high selectivity at temperatures as high as 160° C. or higher.

Example 10: Chlorination of 1243zf with FeCl₃ as Catalyst in Liquid Phase Reactor A 200 ml Hastelloy shaker tube was charged with 3 g of FeCl₃. The reactor was evacuated and purged with N₂ twice, and then chilled to −40° C. At −40° C., the reactor was again evacuated, and 80 g (0.84 mol) 1243zf and 56 g (0.76 mol) Cl₂ was added to the reactor. With agitation the reactor was heated to 40° C. and agitated at 40° C. for 1.5 hour. As the reaction was proceeding, there was a continuous dropping of pressure. By the end of the reaction, the reactor pressure dropped to 7 psig from 112 psig. After the reactor was cooled down back to room temperature, the liquid contents were transferred into a glass jar containing 50 ml 15% NaSO₃ aqueous solution. The organic layer was then separated from the aqueous layer and 122.82 g product was recovered. The product was analyzed using GC-MS. The data reported in Table 11 hereinbelow are indicated by the area percent from the GC-MS. The analysis of liquid phase of the product showed the selectivity to 243db being ~99.8%.

TABLE 11

| Compounds | GC-MS area % |
|---|---|
| 1234yf | 0.014 |
| 1243zf | 7.156 |
| SO2 | 0.028 |
| 243db | 92.653 |
| others | 0.149 |

Example 11: Chlorination of 1243zf with FeCl₃ as Catalyst in Liquid Phase in Autoclave Reactor at 50° C.

Figure 2:
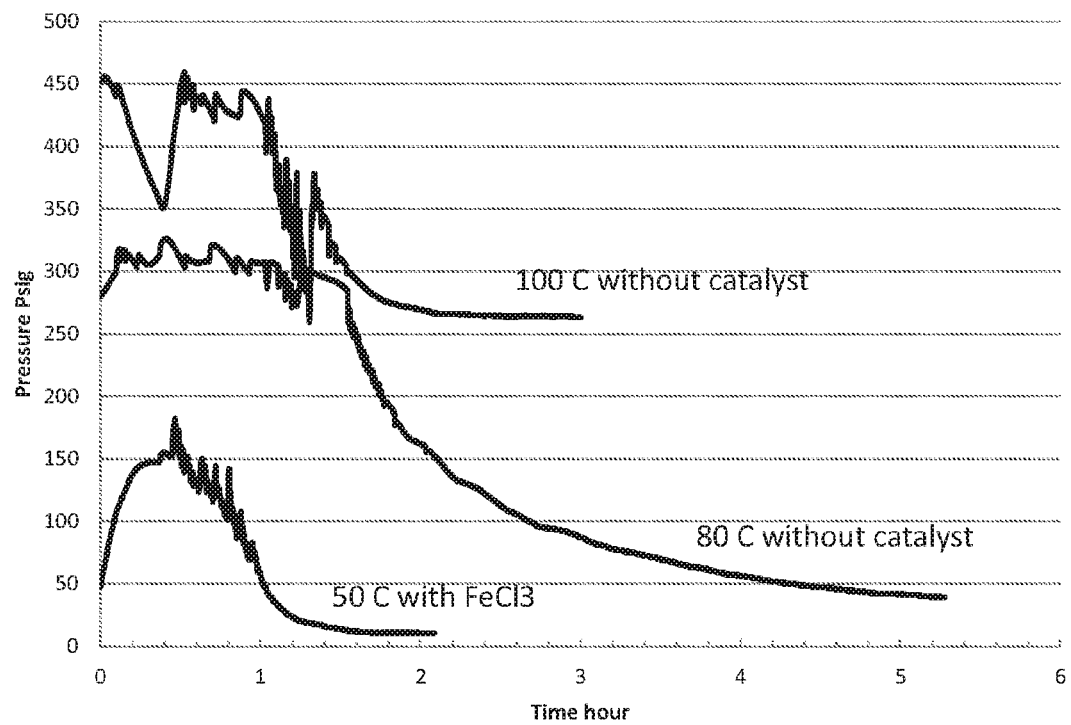
FIG. 2 graphically compares the results of the present process with reactions conducted at higher temperatures and no catalyst present as a function of pressure and time. The lower plot graphically depicts the change in pressure as a function of time for the product formed in accordance with the procedure of Example 11. The middle plot graphically depicts the change in pressure as a function of time for the product formed according to the procedure of Comparative Example 2. The upper plot graphically depicts the change in pressure as function of time for the product formed in accordance with the procedure of Comparative Example 3.

A one liter Hastelloy autoclave was charged with 12.4 g of anhydrous FeCl₃. The reactor was evacuated and purged with N₂ twice, and then chilled to −40° C. At −40° C., the reactor was again evacuated, and 337 g (3.51 mol) 1243zf was added. Then 1243zf was heated to 50° C. with agitation. After that 242 g Cl₂ (3.41 mol) was fed into the reactor at 50° C. in 50 min. After all Cl₂ was added the reaction was agitated another hour at 50° C. As the reaction was proceeding, there was a continuous dropping of pressure. By the end of the reaction, the reactor pressure dropped to 11 psig from 150 psig. The profile of pressure of this reaction is plotted in FIG. 2 (lower plot). The reaction with FeCl$_3$ catalyst is obviously much faster than the reactions in Comparative Examples 2 and 3 without catalyst based on the faster pressure drop. After the reactor was cooled down back to room temperature, the liquid contents were transferred into a glass jar. The 568 g product was recovered and analyzed using GC-MS. The data reported in Table 12 herein below are indicated by the area percent from the GC-MS. The analysis of liquid phase of the product showed the selectivity to 243db being ~99.8%. 243db selectivity with FeCl$_3$ catalyst is also higher than selectivity in Comparative Examples 2 and 3 without a catalyst.

TABLE 12

|  | GC-MS area % |
| --- | --- |
| 1243zf | 3.843 |
| 243db | 95.948 |
| others | 0.209 |

Comparative Example 2: Chlorination of 1243zf without a Catalyst in Liquid Phase in Autoclave Reactor at 80° C.

A one liter Hastelloy autoclave was charged with 12.4 g of anhydrous FeCl$_3$. The reactor was evacuated and purged with N$_2$ twice, and then chilled to −40° C. At −40° C., the reactor was again evacuated, and 338 g (3.52 mol) 1243zf wad added. Then 1243zf was heated to 80° C. with agitation. After that 242 g Cl$_2$ (3.41 mol) was fed into the reactor at 80° C. in 119 min. After all Cl$_2$ was added the reaction was agitated another 3.5 hour at 80° C. As the reaction was proceeding, there was a continuous dropping of pressure. By the end of the reaction, the reactor pressure dropped to 40 psig from 320 psig. The profile with respect to pressure of this reaction is plotted in FIG. 2. The reaction without catalyst at 80° C. (Comparative Example 2, the middle plot) is obviously much slower than the one with FeCl$_3$ at 50° C. in Example 11 (lower plot) based on the slower pressure drop. After the reactor was cooled down back to room temperature, the liquid contents were transferred into a glass jar which contained 100 ml 10% NaSO3 solution. The 568 g product was recovered and analyzed using GC-MS. The data reported in Table 13 herein below are indicated by the area percent from the GC-MS. The analysis of liquid phase of the product showed the selectivity to 243db being ~94.2%. 243db selectivity without a catalyst is lower than selectivity in Example 11 with FeCl$_3$ catalyst.

TABLE 13

|  | GC-MS area % |
| --- | --- |
| 1243zf | 3.057 |
| 243db | 91.297 |
| 233ab | 0.618 |
| 233db | 2.273 |
| others | 2.305 |

Comparative Example 3: Chlorination of 1243zf without a Catalyst in Liquid Phase in Autoclave Reactor at 100° C.

A one liter Hastelloy autoclave was charged with 12.4 g of anhydrous FeCl$_3$. The reactor was evacuated and purged with N$_2$ twice, and then chilled to −40° C. At −40° C., the reactor was again evacuated, and 339 g (3.53 mol) 1243zf wad added. Then 1243zf was heated to 100° C. with agitation. After that 212 g Cl$_2$ (2.98 mol) was fed into the reactor at 100° C. in 84 min. After all Cl$_2$ was added the reaction was agitated another 2 hour at 100° C. As the reaction was proceeding, there was a continuous dropping of pressure. By the end of the reaction, the reactor pressure dropped to 265 psig from 450 psig. The profile of pressure of this reaction is plotted in FIG. 2 (upper plot). The reaction without catalyst at 100° C. is faster than the reaction at 80° C. without catalyst in Comparative Example 2, but is similar to the reaction with FeCl$_3$ at 50° C. in Example 11 based on pressure drop. After the reactor was cooled down back to room temperature, the liquid contents were transferred into a glass jar which contained 100 ml 10% NaSO$_3$ solution. The 439 g product was recovered and analyzed using GC-MS. Black tar was also found in reactor. The data reported in Table 14 herein below are indicated by the area percent from the GC-MS. The analysis of liquid phase of the product showed the selectivity to 243db being ~91.8%. 243db selectivity without a catalyst is lower than selectivity in Example 11 with FeCl$_3$ catalyst.

TABLE 14

|  | GC-MS area % |
| --- | --- |
| 1243zf | 10.717 |
| 243db | 81.93 |
| 233ab | 0.476 |
| 233db | 1.534 |
| others | 5.343 |

Comparative Example 4: Chlorination of 1243zf with Activated Carbon as Catalyst in Liquid Phase in Autoclave Reactor at 60° C.

A 400 ml Hastelloy shaker tube was charged with 3 g activated carbon, 80 g (0.84 mol) 1243zf and Cl$_2$ (54 g 0.76 mol) in the liquid phase. The mixture was agitated at 40° C. for 20 min. The pressure of the reactor stayed at ~160 psig; thus, there was no indication of any reaction taking place. Then the reactor was heated to 60° C. and held at 60° C. for 90 min. The pressure of the reaction only dropped from 236 psig to 200 psig, indicating a very slow reaction. This result shows that activated carbon does not catalyze the chlorination of 1243zf in the liquid phase.

Note that not all of the activities described above in the general description or the examples are required, that a portion of a specific activity may not be required, and that one or more further activities may be performed in addition to those described. Still further, the order in which activities are listed is not necessarily the order in which they are performed.

In the specification, unless indicated to the contrary, the % is by weight.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A composition comprising:
   a. 2,3-dichloro-1,1,1-trifluoropropane (HCFC-243db) at greater than 91 mol %; and
   b. 3,3,3-trifluoro-1-propene (HFO-1243zf) at between about 3 to about 7 mol %;
   wherein the composition is a reactor product liquid stream.

2. The composition of claim 1 wherein the HCFC-243db is present in an amount between about 92 mol % and about 96 mol %.

3. The composition of claim 1 further comprising 2,3,3,3-tetrafluoropropylene (HFO-1234yf).

4. The composition of claim 3 wherein the HFO-1234yf is present at up to about 0.015 mol %.

5. The composition of claim 1 further comprising at least one member selected from the group consisting of HCFC-1233xf, HCFC-1233zd, HCFC-233ab, HCFC-233da, HCFC-1223xd, HCFC-223aa, HCFC-1213xa, HCFC-213ab, HCFC-244db and HCFC-242dc.

6. A composition comprising HCFC-243db, chlorine, and at least one chlorination catalyst, wherein the chlorination catalyst comprises a metal chloride.

7. The composition of claim 6, wherein the metal chloride comprises a metal from Group 13, 14 or 15 of the periodic table or a transition metal or combination thereof and the metal chloride is supported on activated carbon.

8. The composition according to claim 6 further comprising 3,3,3-trifluoropropene.

9. The composition according to claim 7 wherein the activated carbon is caustic washed.

10. The composition of claim 8, wherein the catalyst is present in an amount ranging from about 0.1 to about 10 wt% of the total weight of chlorine and 3,3,3-trifluoropropene.

11. The composition according to claim 7 wherein the activated carbon is acid washed.

12. The composition according to claim 7 wherein the metal is nickel, chromium, iron, scandium, yttrium, lanthanum, titanium, zirconium, hafnium, vanadium, molybdenum, tungsten, manganese, rhenium, ruthenium, osmium, cobalt, palladium, copper, zinc, tantalum, aluminum, tin, or lead.

13. The composition according to claim 7 wherein the metal chloride is nickel chloride, iron chloride, or chromium chloride.

14. The composition according to claim 10 wherein the mole ratio of 3,3,3-trifluoropropene to chlorine ranges from about 1:0.02 to about 1:1.

15. The composition according to claim 14 wherein the mole ratio of 3,3,3-trifluoropropene to chlorine ranges from about 1:0.1 to about 1:0.8.

16. The composition according to claim 14 wherein the mole ratio of 3,3,3-trifluoropropene to chlorine ranges from about 1:0.1 to about 1:0.5.

17. The composition according to claim 7 wherein a solvent is additionally present said solvent being carbon tetrachloride, 1,1,2-trichloro-1,2,2-trifluoroethane, a $C_{5-8}$ linear perfluoroalkyl compound represented by $CF_3(CF_2)_nCF_3$, where n is an integer from 3 to 6, inclusive, or a hexachloracetone.

* * * * *